United States Patent [19]

Nishimura et al.

[11] Patent Number: 5,038,035
[45] Date of Patent: Aug. 6, 1991

[54] AUTOMATIC STRUCTURE ANALYZING/PROCESSING APPARATUS

[75] Inventors: Nobuhiko Nishimura; Fujimitsu Masuyama; Akira Kaneko, all of Nagasaki, Japan

[73] Assignee: Mitsubishi Jukogyo Kabushiki Kaisha, Tokyo, Japan

[21] Appl. No.: 376,664

[22] Filed: Jul. 6, 1989

[30] Foreign Application Priority Data

Aug. 5, 1988 [JP] Japan ............... 63-196287

[51] Int. Cl.⁵ ............................................. G01N 23/04
[52] U.S. Cl. ..................................... 250/311; 250/310; 359/372; 359/391; 359/368
[58] Field of Search ............... 250/311, 306, 310; 350/502, 508, 518, 519, 526, 528, 529, 511

[56] References Cited

U.S. PATENT DOCUMENTS

| | | | |
|---|---|---|---|
| 4,366,380 | 12/1982 | Mirkin | 250/306 |
| 4,385,317 | 5/1983 | Furuya et al. | 250/311 |
| 4,468,560 | 8/1984 | Kubozoe et al. | 250/311 |
| 4,523,094 | 6/1985 | Rossow | 250/311 |
| 4,680,469 | 7/1987 | Nomura et al. | 250/311 |
| 4,695,725 | 9/1982 | Mori et al. | 250/311 |
| 4,777,523 | 10/1988 | Yokoto et al. | 250/311 |
| 4,788,426 | 11/1988 | Kuehnle | 250/311 |
| 4,789,780 | 12/1988 | Le Poole et al. | 250/311 |
| 4,820,921 | 4/1989 | Bakker et al. | 250/311 |
| 4,866,273 | 9/1989 | Kobayashi et al. | 250/311 |
| 4,872,052 | 10/1989 | Liudzius et al. | 350/311 |

Primary Examiner—Jack I. Berman
Assistant Examiner—Kiet T. Nguyen

[57] ABSTRACT

An automatic structure analyzing/processing apparatus for surface structure of material includes a structure observing device for observing structure of a surface of material to produce an electrical image signal thereof, a sample stage disposed opposite to the observing means an image processing device for converting the image signal from the structure observing device to digital signal and expanding or contracting a desired image reproduced from a memory means or combining a plurality of images reproduced from the memory means to produce an image signal, the memory device storing the digital signal processed by the image processing device, and a display device for displaying the image signal produced from the image processing device as an image, whereby the structure of the surface of material is stored in the memory as the image and examination of the structure can be made readily in a short time.

4 Claims, 3 Drawing Sheets

AUTOMATIC STRUCTURE ANALYZING/PROCESSING APPARATUS

FIELD OF THE INVENTION AND RELATED ART STATEMENT

The present invention relates to an automatic structure analyzing/processing apparatus for use in material investigation and inspection for mechanical components and the like.

A conventional structure analyzer such as an optical microscope or an electron microscope is used to observe and record a structure in a field of vision having a certain magnification in an area to be examined.

However, since a conventional structure analyzer can observe only one field of a time it first observes a wide area at a low magnification and then observes each portion of the structure with a high magnification. In this case, it is necessary to move the location of the structure to be examined to the, center in the field of the analyzer while observing the structure and magnification, and then observe the location of the structure is then observed with a high magnification while gradually increasing the magnification.

Further, when there are many locations to be examined in a same sample, it is necessary to look for the individual locations and take the respective photographs of the locations. In order to understand a relative positional relation among the individual locations to be examined, it is necessary to read the individual locations from the respective scales in the X-axis and Y-axis of a goniometer or a micrometer attached to a sample stage and to write the read locations on a section paper.

In the storage of data examined, it is necessary to take a photograph thereof and keep the photograph or a film thereof in custody. Accordingly, much space is required for the custody. When the data is required later, it is necessary to look for it from the data kept in the custody.

OBJECT AND SUMMARY OF THE INVENTION

The present invention has been made in view of the above problems and an object of the present invention is to solve the above problems and to provide an automatic structure analyzing/processing apparatus capable of readily and automatically recording (or storing) an image of structure of a surface of material to be examined in a short time.

It is another object of the present invention to provide an automatic structure analyzing/processing apparatus capable of examining structure of material from the recorded (or stored) image in a short time and readily.

In order to achieve the above objects, the automatic structure analyzing/processing apparatus according to the present invention comprises structure observing means for observing structure of a surface of material to produce an electrical image signal thereof, a sample stage disposed opposite to the observing means, image processing means for converting the image signal from the structure observing means to digital signal and expanding or contracting a desired image reproduced from a memory means or combining a plurality of images reproduced from the memory means to produce an image signal, the memory means storing the digital signal processed by the image processing means and display means for displaying the image signal produced from the image processing means as an image.

More particularly, the apparatus comprises a motor for driving a sample stage of a structure analyzing apparatus such as a conventional optical microscope, a computer for controlling the motor and positioning a small fractionated area of an area to be examined of a sample in a field of the optical microscope, an automatic focus adjusting mechanism, a digital signal memory such as an optical disk including a combined image storing and reproducing mechanism for forming a continuous image consisting of fractionated images corresponding to the small fractionated areas on the sample to be examined and digitizing the continuous image by an image processing device to store the digitized image signal, the image processing device combining stored images of any small areas of all of the small areas to produce the combined images in a desired position with any magnification, and a display device for displaying the combined images as a single image.

In operating the automatic structure analyzing apparatus according to the present invention for observing structure of material, a predetermined area to be observed on a surface of the material is fractionated into small areas each having any identical shape such as, for example, a square and each of the small areas is marked. Structure of each of the small areas is observed by an optical microscope or an electron microscope with a television camera having an automatic focus adjusting function and an image of each of the small areas is produced as an electrical signal, which is digitized by the image processing device to be stored in the digital signal memory such as an optical disk together with a mark of the small area. The sample stage is then moved to a next small area by the motor controlled by a computer, and an image thereof and a mark indicating a position of the image are stored by the above operation. Such an operation is repeated for all of the small areas and image signals of all of the small areas for the whole area to be observed are stored in the memory. all or a part of the images of all of the small areas in the area to be observed are continuously displayed on the display device. Thus, the whole image or a partial detailed image of the area to be observed is automatically observed.

As described above, according to the present invention, the automatic structure analyzing/processing apparatus can automatically record (or store) an image of structure of material readily in a short time instead of the conventional analysis of the structure of material in which a point to be photographed of the structure of material is determined while the observer observes the structure by a microscope and many photographs of such points are taken. Accordingly, examination of the structure of material which is made in the quality control of material can be made readily in a short time.

Further, since the observed image can be stored in a memory such as an optical disk, the effective custody and smooth search of data are possible and a data base for structure of material can formed.

BRIEF DESCRIPTION OF THE DRAWINGS

FIGS. 3 to 5 illustrate images of structure obtained by an embodiment of the present invention, in which FIG. 3 shows a structure of cracked steel in an observation area having 10 mm × 10 mm formed by combining 2500 images each magnified to 300 times, FIG. 4 shows a structure of an area indicated by a reference 13 in FIG. 3 and formed by combination of 10 × 10 images each magnified to 300 times and FIG. 5 shows a structure of an area indicated by a reference 15 in FIG. 4 and corresponding to an image magnified to 300 times.

DETAILED DESCRIPTION OF PREFERRED EMBODIMENTS

An embodiment of the present invention is described with reference to FIGS. 1 to 5.

Figure 1:
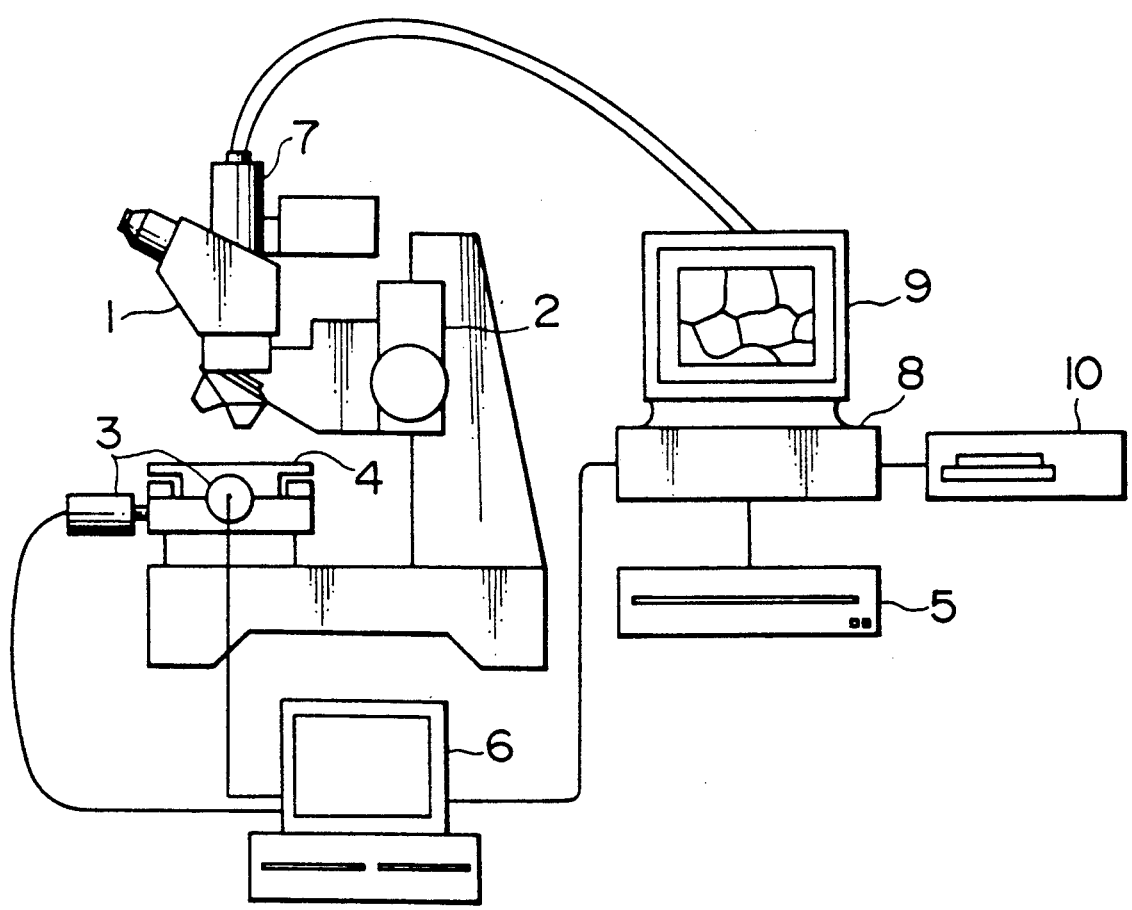
FIG. 1 schematically illustrates an automatic structure analyzing/processing apparatus according to an embodiment of the present invention.

FIG. 1 schematically illustrates an automatic structure analyzing/processing apparatus. In FIG. 1, numeral 1 denotes an optical microscope, to which an automatic focus adjusting mechanism 2 and a sample stage 4 controlled in X-axis and y-axis direction and having two set of gears and motors 3 having a positioning accuracy of ±1 μm are mounted. The apparatus of FIG. 1 includes a computer 6 connected to the microscope 1 for moving the stage 4 by any amount of movement in the directions of the X and Y axes at any intervals of time to control a position of the stage 4 and storing information of a relative position of the stage 4 calculated back from the amount of movement into a memory 5, and a television camera 7 connected to the microscope 1 for taking an image of structure of a surface of material magnified by the optical microscope. Further, connected to the television camera 7 is an image processing device 8 which digitizes an electrical image signal and effects expansion or contraction of an image reproduced from the memory 5 or combination thereof to produce its image signal. The image processing device 8 is further connected to a display 9, which displays, and a printer 10 which prints, the image signal from the image processing device 8 as an image.

Figure 2:
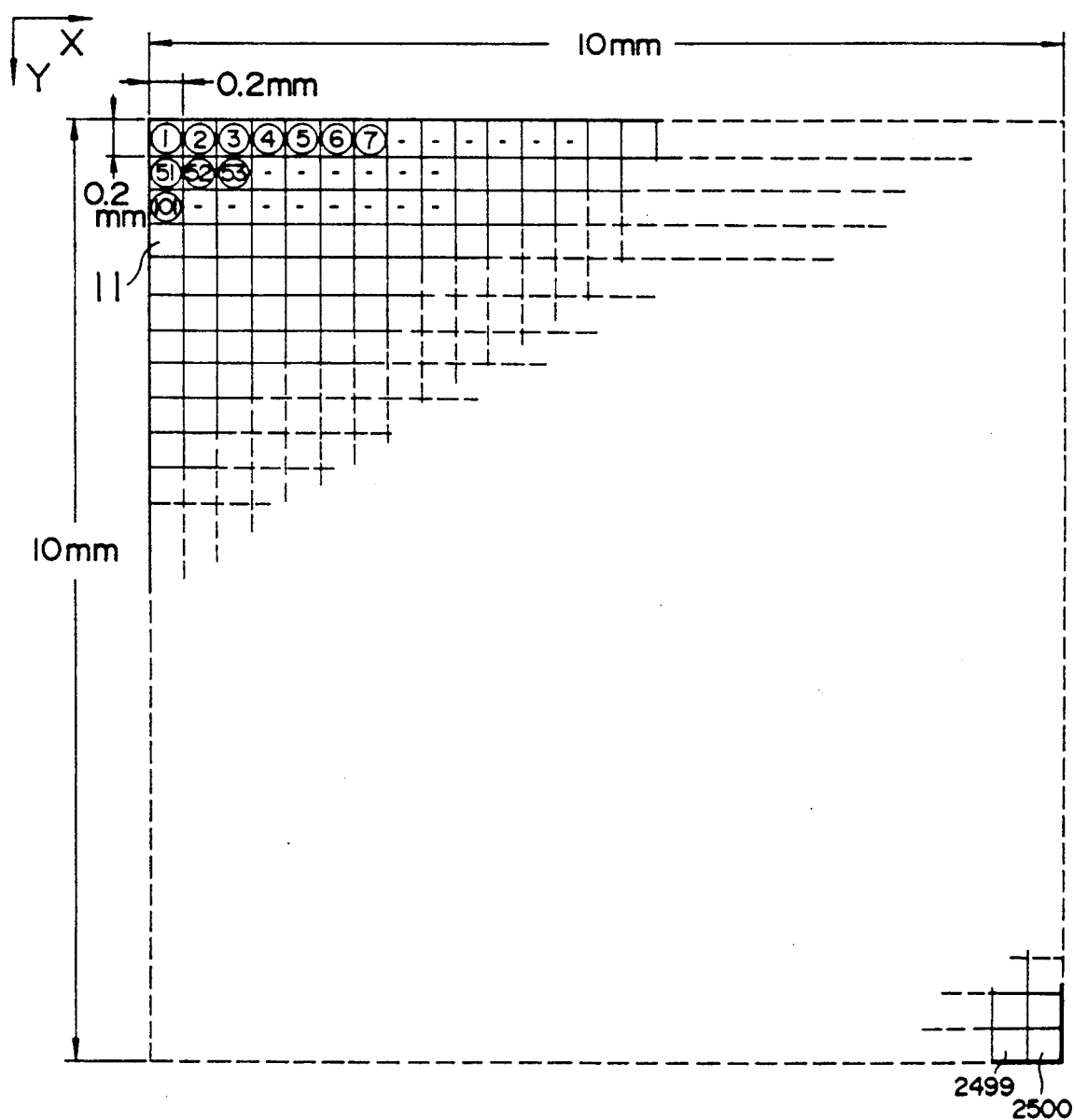
FIG. 2 illustrates a method of recording images in a wide area according to an embodiment of the present invention.

The apparatus shown in FIG. 1 has been used to analyze structure of material used for a long time as a mechanical component. As shown in FIG. 2, an area to be observed is a square area having 10 mm × 10 mm, which is fractionated vertically and horizontally into a plurality of small areas 11 having dimensions 0.2 mm × 0.2 mm. Then, the small areas 11 are marked with ①, ②, ③, ... starting from the upper left corner to the lower right corner in order and the relation of the small area and the marks is stored in the computer 6. An observation position at the upper left corner is determined with the optical microscope 1 and an image magnified to 300 times by the microscope of structure of the small area 11 marked by ① is taken by the television camera 7 to supply it to the image processing device 8 as an electrical image signal, which is digitized to be stored in the memory 5 such as an optical disk together with the mark ① of the small area 11. Then, the sample is moved 0.2 mm in the X-axis direction of FIG. 2 together with the sample stage 4 by the computer 6 so that the observation position of the optical microscope 1 is positioned to the small area 11 marked by ② in FIG. 2. An image of structure of the small area 11 marked by ② is stored in the memory 5 together with the mark ② in the same manner as described above. The above operation is repeated 50 times to store the images of structure within 10 mm in the X-axis direction. Then, the sample is moved 0.2 mm in the Y-axis direction and 9.8 mm in the reverse direction to the X-axis direction together with the sample stage 4 by the computer 6 so that the observation position of the optical microscope 1 is positioned to the small area 11 marked by 51 of FIG. 2. Images of structure of 50 small areas 11, which are magnified to 300 times by the microscope, are successively taken in the same manner as above and stored as image signals in the memory 5. With repetition of the above operation, the sample is moved 9.8 mm by 0.2 mm in the Y-axis direction while 50 images of structure are taken in the X-direction for each movement of 0.2 mm in the Y-axis direction so that the recording operation is completed.

A display screen of the display device 9 is fractionated into 50 × 50 small areas in the same manner as shown in FIG. 2 and the images of structure taken by the optical microscope and stored in the memory 5 are displayed on the small areas of the display 9 to combine all of the images into a signal image.

Figure 3:
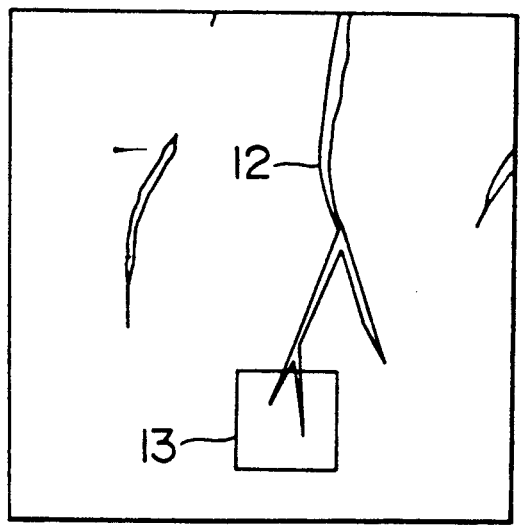

FIG. 3 shows an image printed by the printer 10 of the combined image as described above. A broad distribution of cracked portions 12 in the component can be confirmed as shown in FIG. 3.

Then, in order to enlarge only the structure of an area 13 containing ends of the crack portion in FIG. 3, the mark corresponding to the area 13 is detected by the computer 6 and 10 × 10 images corresponding to the area 13 are displayed on 10 × 10 fractionated square areas on the display device 9 on an enlarged scale in the correspondence manner.

Figure 4:
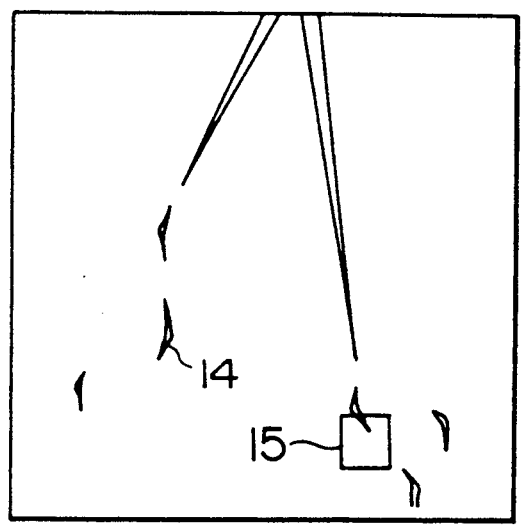

FIG. 4 shows the enlarged image as obtained above. As can be seen from FIG. 4, it can be confirmed that there are many small cracks 14 at the end of the cracked portion 12 which could not be confirmed in the image shown in FIG. 3.

Further, in order to examine only structure in an area 15 containing an end of the small crack in FIG. 4, the mark corresponding to the area 15 is detected by the computer 6 and only one image of the area 15 is displayed on the whole area of the display device 9 on an enlarged scale.

Figure 5:
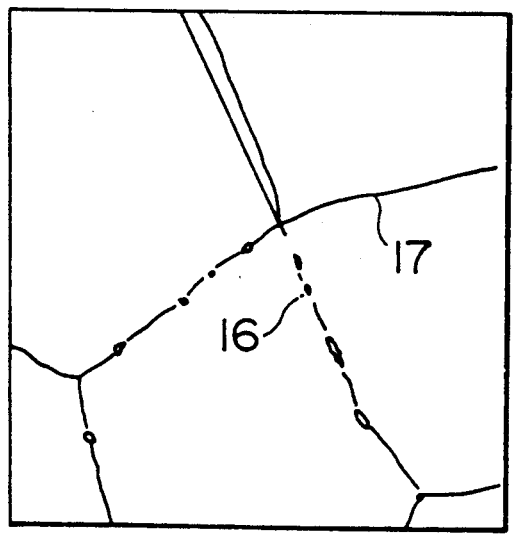

FIG. 5 shows the enlarged image as obtained above. It can be confirmed that there exist many small cavities 16 on a crystal grain boundary 17 in the end of the small crack which could not be confirmed in the image shown in FIGS. 3 and 4.

Because the apparatus according to the present invention includes the automatic focus adjusting mechanism, structure having unevenness can be observed. Further, a small defect in a silicon wafer of a semiconductor or an optical disk, which can not be detected by a structure analyzer having a low magnification, can be inspected over a broad area and a position thereof can be displayed so that the apparatus of the present invention can be applied as a defect detector.

We claim:

1. An automatic structure analyzing and processing apparatus for observing the surface structure of material, which comprises:
   (a) structure observing means having an automatic focus adjusting mechanism to automatically focus on the surface of a structure and for outputting an image of the automatically focused surface of the structure as an electric image signal;
   (b) a sample stage for holding the structure relative to said structure observing means, said sample stage having motors for moving the structure along;

(c) control means for dividing a predetermined observation area of the surface of said structure into a plurality of small areas, controlling the motors of said sample stage in order to set said small areas in the position for observation by said structure observing means so that said observing means focuses on one small area at a time with a given magnification, and outputting their respective position data;

(d) memory means for storing data;

(e) image processing means for digitizing image signals from said structure observing means so as to output said digital signals to said memory means and for combining a plurality of mutually adjacent memorized images of said small areas to obtain an image of a magnification less that the given magnification and outputting said combined image as an image signal;

(f) said memory means serving to memorize said digital image signal produced by said image processing means in relation with said position data output from said control means; and (g) display means for displaying said image signal produced by said image processing means as an image.

2. An automatic structure analyzing and processing apparatus according to claim 3, wherein said structure observing means comprises an optical microscope having a television camera.

3. An apparatus as in claim 1, wherein said structure observing means includes an electron microscope having a television camera.

4. An apparatus for analyzing an area on the surface of a sample, comprising:

a camera for producing images;

a support for holding a sample to be analyzed opposite said camera and for moving the sample so as to expose respective subdivisions of the area to be analyzed;

focusing means in the camera for focusing on the respective subdivisions which the support exposes to the camera at a given magnification;

memory means for storing the digitized images; display means for displaying images;

image processing means for digitizing images of a subdivision upon which the camera focuses and giving each digitized image an address and storing the images and addresses in said memory means, and for selectively retrieving a plurality of stored digitized images representing adjacent subdivisions, and simultaneously displaying said plurality of retrieved adjacent plurality of stored digitized images as a composite image corresponding to the adjacent subdivisions at a magnification less than the given magnification.

* * * * *